US011360004B2

(12) United States Patent
Choi et al.

(10) Patent No.: US 11,360,004 B2
(45) Date of Patent: Jun. 14, 2022

(54) SHALE GAS EXTRACTING DEVICE AND EXTRACTING METHOD THEREFOR

(71) Applicant: KOREA INSTITUTE OF GEOSCIENCE AND MINERAL RESOURCES, Daejeon (KR)

(72) Inventors: Jiyoung Choi, Daejeon (KR); Ji-Hoon Kim, Daejeon (KR); Joo Yong Lee, Daejeon (KR)

(73) Assignee: KOREA INSTITUTE OF GEOSCIENCE AND MINERAL RESOURUES, Daejeon (KR)

( * ) Notice: Subject to any disclaimer, the term of this patent is extended or adjusted under 35 U.S.C. 154(b) by 142 days.

(21) Appl. No.: 16/646,260

(22) PCT Filed: Sep. 12, 2018

(86) PCT No.: PCT/KR2018/010669
§ 371 (c)(1),
(2) Date: Mar. 11, 2020

(87) PCT Pub. No.: WO2019/054738
PCT Pub. Date: Mar. 21, 2019

(65) Prior Publication Data
US 2020/0284699 A1 Sep. 10, 2020

(30) Foreign Application Priority Data
Sep. 15, 2017 (KR) .................... 10-2017-0118863

(51) Int. Cl.
*G01N 1/22* (2006.01)
*G01N 1/24* (2006.01)
*G01N 33/22* (2006.01)

(52) U.S. Cl.
CPC .......... *G01N 1/2294* (2013.01); *G01N 1/2214* (2013.01); *G01N 1/24* (2013.01); *G01N 33/225* (2013.01); *G01N 2001/248* (2013.01)

(58) Field of Classification Search
CPC ...... G01N 1/2294; G01N 1/2214; G01N 1/24; G01N 2001/248
(Continued)

(56) References Cited

U.S. PATENT DOCUMENTS 7,953,585 B2   5/2011  Gurpinar et al.
2010/0314235 A1  12/2010  Varadaraj et al.
(Continued)

FOREIGN PATENT DOCUMENTS

KR    20-2000-0021407    12/2000
KR       10-0321064       1/2002
(Continued)

OTHER PUBLICATIONS

KIPO, PCT Search Report & Written Opinion of PCT/KR2018/010669 dated Dec. 21, 2018.
(Continued)

*Primary Examiner* — Robert R Raevis
(74) *Attorney, Agent, or Firm* — Lex IP Meister, PLLC (57) ABSTRACT

The present invention relates to a shale gas extracting device, and provides a shale gas extracting device comprising: a canister, which is vertically and rotatably provided on a canister support vertically provided on both sides of a base, has an receiving space for accommodating a drilled rock sample and a ball mill together in a sealed manner, and has an injection opening at one side of a top thereof; a driving means for vibrating the canister such that the rock sample is crushed by mixing with the ball mill accommodated in the canister; a heating means for heating the canister; and a vacuum pipe, a pressure pipe, a sensor pipe, an injection
(Continued)

pipe and an extracting pipe sequentially and detachably coupled to the injection opening of the canister.

9 Claims, 8 Drawing Sheets

(58) Field of Classification Search
USPC .............. 73/863, 864, 19.01, 19.12, 863.11, 73/863.12, 863.21, 863.83, 864.34, 73/864.81
See application file for complete search history.

(56) References Cited

U.S. PATENT DOCUMENTS

| | | |
|---|---|---|
| 2010/0320120 A1 | 12/2010 | Siskin et al. |
| 2013/0346040 A1 | 12/2013 | Morales German et al. |
| 2014/0332207 A1 | 11/2014 | Hinkel et al. |
| 2014/0378319 A1 | 12/2014 | Regberg et al. |
| 2015/0039544 A1 | 2/2015 | Gupta et al. |
| 2015/0240633 A1 | 8/2015 | Akkurt et al. |
| 2016/0139293 A1 | 5/2016 | Misra et al. |
| 2016/0334347 A1 | 11/2016 | Valori et al. |

FOREIGN PATENT DOCUMENTS

| | | | |
|---|---|---|---|
| KR | 10-1341444 | | 12/2013 |
| KR | 10-1593895 | | 2/2016 |
| KR | 10-2016-0035186 | | 3/2016 |
| KR | 10-2016-0043620 | | 4/2016 |
| KR | 10-1625660 | | 5/2016 |
| KR | 10-1646988 | | 8/2016 |
| WO | 2012-036783 | | 3/2012 |
| WO | 2012-036784 | | 3/2012 |
| WO | 2012-071103 | | 5/2012 |
| WO | 2012-154846 | | 11/2012 |
| WO | 2016-011384 | | 1/2016 |
| WO | 2018/111945 | * | 6/2018 |

OTHER PUBLICATIONS

A. G. Journel, "Combining Knowledge From Diverse Sources: An Alternative to Traditional Data Independence Hypotheses", Mathematical Geology, vol. 34, No. 5, Jul. 2002.

Paulo Chaves et al., "Operation of storage reservoir for water quality by using optimization and artificial intelligence techniques", Mathematics and Computers in Simulation 67 (2004) 419-432.

Shahab Dean Mohaghegh, "Reservoir simulation and modeling based on artificial intelligence and data mining (AI&DM)", Journal of Natural Gas Science and Engineering 3 (2011) 697-705.

Yuqing Chang et al., "Integrated Work Flow of Preserving Facies Realism in History Matching: Application to the Brugge Field", Aug. 2016 SPE Journal, 1413-1424.

* cited by examiner

SHALE GAS EXTRACTING DEVICE AND EXTRACTING METHOD THEREFOR

TECHNICAL FIELD

The present invention relates to a shale gas extracting device, and more specifically, to a shale gas extracting device and extracting method therefor for extracting shale gas under the same pressure and temperature conditions as the shale layer in order to measure the accurate shale gas reserve in a rock sample of the drilled shale layer.

BACKGROUND ART

In general, shale gas is a natural gas buried in the shale layer, which is a sedimentary rock layer in which sand and mud are hardened, and is buried in a deeper layer than natural gas currently commonly drilled.

The above-mentioned shale layer is an aqueous rock formed by hardening of clay, has a gray or blackish brown color, and is often a thin layer that is easily peeled off. The shale layer contains excess amounts of nitrogen and sulfur compounds so that it has a different purification method from that of a petroleum. Therefore, in the refining process, shale gas can be obtained only through hydrocracking process. The organic components obtained therefrom generally have less naphtha, and contain oil components suitable for producing light oil or kerosene.

The shale gas extracting method was first developed in England in 1694 and the shale gas had been produced with an limited amount around a world. In oil shock of 1973, interest of the shale gas and oil increased.

In addition, as the price of oil produced in oil producing countries in the Middle East including Saudi Arabia has continued to rise, the shale gas has gained commercial productivity with the development of new drilling methods. In the United States where production technology has been secured, large scaled development had begun since 1980s.

Furthermore, the shale layer is distributed in many countries, including China, Russia, United States, Canada, Mexico, Australia, France, Brazil, Argentina, and it is estimated that a large amount of reserves that can be mined in the coming decades. China has the largest reserves in the world. One of the reservoir factors for developing shale gas is the accurate measurement of the amount of gas contained within the reservoir. The reservoir means a layer of crude oil or natural gas piled up in the underground.

For this purpose, the shale gas is measured through rock samples by directly or indirectly using drilling cores. Indirect methods indirectly measure the amount of shale gas remaining in the shale layer by using gas adsorption and desorption isotherm measurement data in the laboratory, related statistics, gas content inference data from degree of carbonization, density verification measurements, and data relationship between density and gas content.

The direct method is to gain in-situ rock samples by drilling in the field, and to measure an amount of gas desorbed from the sample and the gas desorption rate. This method has higher reliability than the indirect method.

The amount of the shale gas measured by the direct method includes the amount of lost gas generated during drilling and transportation of the rock samples, the amount of desorbed gas generated during desorption, and the amount of residual gas remaining in the core after desorption, and the total gas content is the sum of these three measurements.

The residual gas volume is measured by crushing the rock sample and checking the amount of shale gas remaining in the rock sample. In other words, the amount of residual gas is to measure the amount of gas relative to the crushed weight of the rock sample.

In this case, if the crush rate of the rock sample is low, considerable amount of residual gas remained in the rock sample is not discharged from the rock sample. Thus, the reliability of the measured residual gas amount becomes very low, so that the rock sample is crushed to the extent that the rock sample is penetrated into the wire netting of 60 mesh.

However, there are residual gases that are trapped in the internal air gaps of the crushed rock sample. The air gap, vacancy between soil particles, is one of the physical properties of the soil. That is, in order to further increase the reliability, a technique for extracting residual gas that has not escaped from the crushed rock sample material is required.

In this regard, KR10-1646988B1 discloses a system for extracting methane gas from the air gap including a cylindrical canister, in which a rock or sediment drilled by a drilling core and a rod mill are inserted hermetically; a power unit for rotating the canister; and a heating device for heating the canister. It is possible to extract the residual gas trapped in the internal micro-pores of the core sample, which was not discharged to the outside by the head space method even if the core sample is crushed. Although the system for extracting methane gas in the air gap has an effect of increasing the reliability of the measured residual gas amount, more accurate measurement of the amount of shale gas is required. Unlike the existing rotational manner, as the structure is changed to the inducing manner, it is required to secure economic efficiency by minimizing the volume.

DISCLOSURE

Technical Problem

Reflecting the required conditions as described above, the drilled rock sample is sealed in the canister together with the ball mill in the present invention. The canister is oscillated by a electrically connected crank rod while maintaining the same conditions as the shale layer. Then, extracting amount of the shale gas is analyzed and accurate reserves of the reservoir can be confirmed. The purpose of the present invention is to provide a shale gas extracting device and a method thereof which can secure profitability and minimize the volume by changing the structure into the inducing manner which is different from the conventional rotational manner.

Technical Solution

In order to achieve the above object, the present invention is to provide a shale gas extracting device including a canister installed on a canister support vertically installed on both sides of a base so as to be vertically rotatable, forming a receiving space for hermetically receiving the drilled rock sample and the ball mill together and having an injection port at one side of an upper end of the canister; driving means oscillating the canister 200 so that the rock sample is crushed by mixing with the ball mill accommodated in the canister; heating means heating the canister; and a vacuum tube, a pressure tube, a sensor tube, an injection tube, and a collecting tube sequentially detached and coupled to the injection port of the canister.

Here, the driving means includes a driving motor installed on the base and having a rotational power; a crankshaft installed in the base, being adjacent to the driving motor and driven to rotate by being connected to the driving motor; and a connecting rod connected to the crank shaft and a bracket formed in a lower portion of the canister and then is driven by a rotation of the crank shaft.

At this time, the vacuum tube is detachably connected to the injection port of the canister so as to suction and remove atmospheric gas and then evacuate the receiving space of the canister. The pressure tube is detachably connected to the injection port of the canister so as to inject nitrogen gas into the receiving space of the canister and increase an internal pressure of the receiving space. The injection tube is detachably connected to the injection port of the canister so as to inject a supersaturated sodium chloride solution into the receiving space of the canister and then separate the shale gas from the rock sample. The extracting tube is detachably connected to the injection port of the canister so as to suction and collect the shale gas separated from the rock sample.

Meanwhile, a check valve is further provided to prevent leakage of materials and pressure received and injected into the receiving space. The check valve is installed in the injection port.

In addition, in a method for collecting shale gas using the above-identified shale gas extracting device, the method provides a step of injecting the drilled rock sample and the ball mill together into the receiving space of the canister and hermetically receiving the drilled rock sample and the ball mill; a step of removing the atmospheric gas in the canister by connecting the vacuum tube to the injection port of the canister; a step of providing the same environmental conditions as the shale layer with an inside of the canister; a step of maintaining an internal environment of the canister by feedback through a sensor connected to the canister; a step of crushing the rock sample with the ball mill by oscillating the canister which is driven by the driving means; a step of injecting a supersaturated sodium chloride solution into the canister by connecting the injection tube to the injection port of the canister; and a step of collecting the shale gas separated from the rock sample by connecting the extracting tube to the injection inlet of the canister.

At this time, the step of providing includes a step of pressurizing the receiving space of the canister so as to increase a pressure of the receiving space by connecting the pressure tube to the injection port of the canister and injecting nitrogen gas into the receiving space of the canister; and a step of heating the receiving space of the canister through the heating means provided outside of the canister.

By providing the present invention configured as described above, the exact reserve of the reservoir can be confirmed by analyzing the amount of shale gas from the drilled rock sample. As the structure of the shale gas extracting device is changed to the inducing manner unlike the conventional rotational manner, there is an effect of securing profitability by minimizing the volume.

| Reference Numerals | |
|---|---|
| 10. rock sample | 20. ball mill |
| 100. base | 120. canister support |
| 121. frame | 123. support bars |
| 200. canister | 200a. body |
| 200b. lid | 201. bracket |
| 203. support shaft | 210. receiving space |
| 220. injection port | 221. check valve |
| 230. vacuum tube | 230. pressure tube |
| 250. sensor tube | 251. sensor |
| 260. injection tube | 270. extracting tube |
| 300. driving means | 310. driving motor |
| 320. crank shaft | 330. connecting rod |
| 400. heating means | S100. step of injecting |
| S200. step of removing | S300. step of providing |
| S310. step of pressurizing | S320. step of heating |
| S400. step of maintaining | S500. step of crushing |
| S600. step of injecting | S700. step of collecting |

BEST MODE

Hereinafter, exemplary embodiments of the present invention will be described in detail with reference to the accompanying drawings so that those skilled in the art may easily implement the present invention.

As shown in FIGS. 1 to 7, the shale gas extracting device of the present invention is provided with a panel-shaped base 100, and a driving means 300 is installed on the base 100. The canister 200 is spaced apart from the driving means 300 by the upper canister support 120, and the canister 200 is oscillated by driving the driving means 300. Then, the rock sample 10 sealed in the receiving space 210 is crushed by the ball mill 20, thereby the shale gas is collected.

In the above configuration, the canister 200 is rotatably arranged vertically to the canister support 120 installed vertically on both sides of the base 100. A receiving space 210 is formed to hermetically receive the drilled rock sample 10 and the ball mill 20 together. The canister 200 has an injection hole 220 at one side of the upper end thereof.

Figure 1:
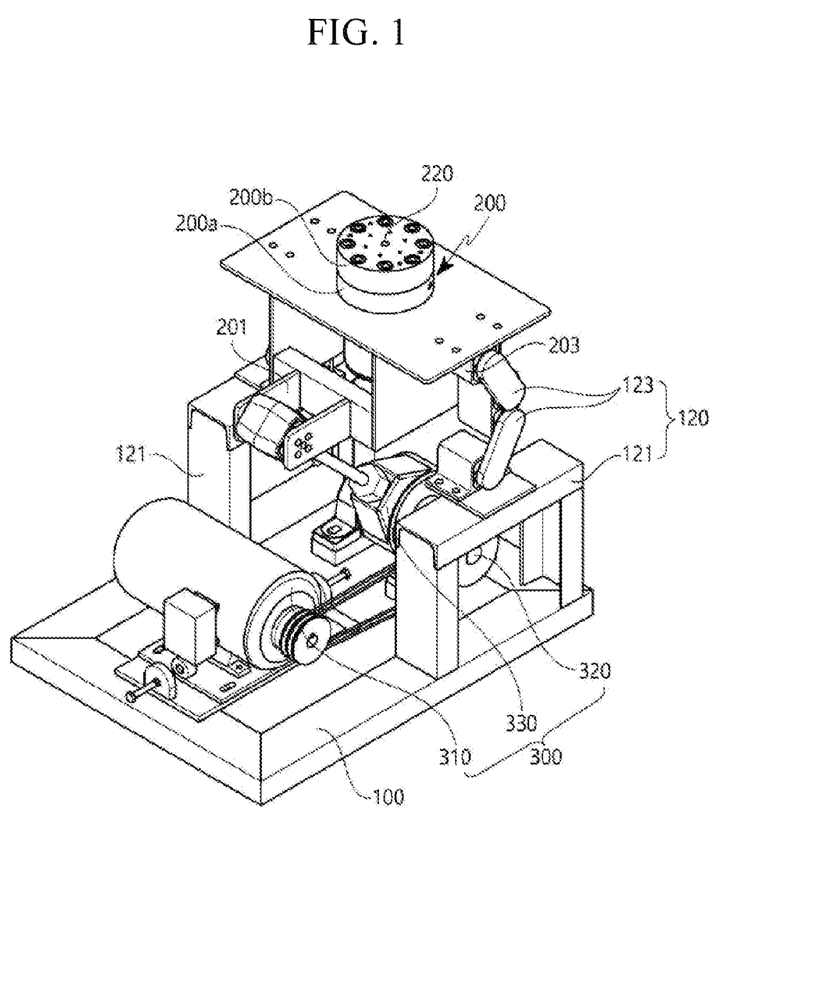
FIG. 1 is a diagram showing a shale gas extracting device according to the present invention.
Figure 2:
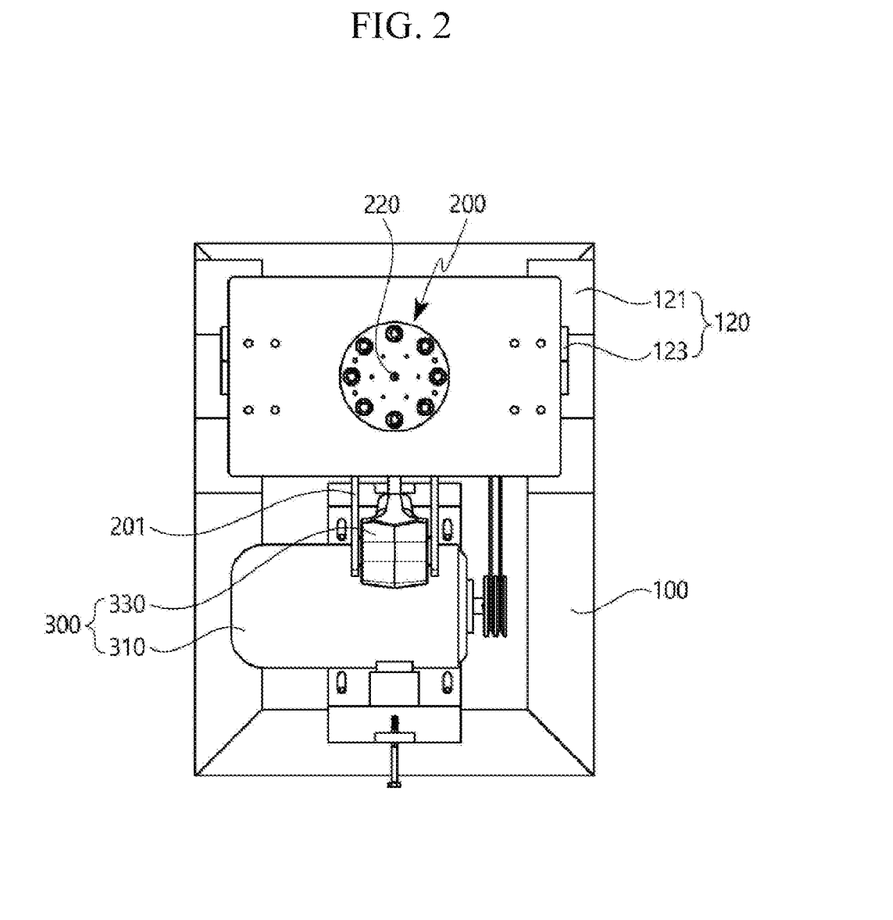
FIG. 2 is a plan view showing a shale gas extracting device according to the present invention.
Figure 3:
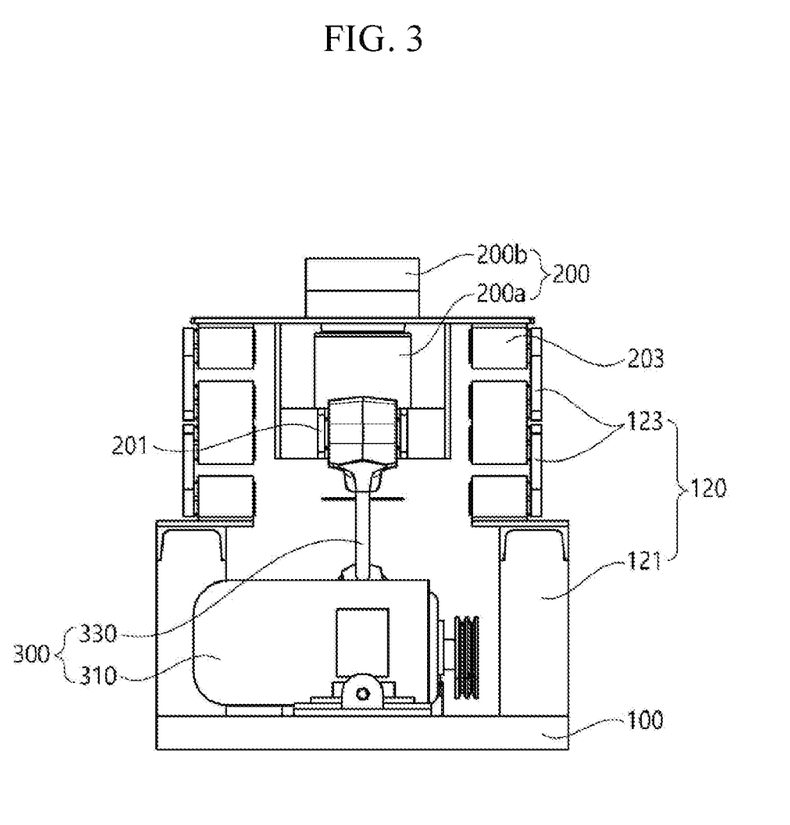
FIG. 3 is a front view showing a shale gas extracting device according to the present invention.

At this time, as shown in FIGS. 1 and 3, the canister support 120 is formed on both sides with respect to the canister 200, respectively. The frame 121 is vertically extended to the upper side of the base 100 and link the two support bars 123 to the upper part of the frame 121, and connect the ends thereof to the support shafts 203 formed around the canister 200 in the longitudinal direction as a watermill. It is preferable to be installed to rotate freely.

Figure 5:
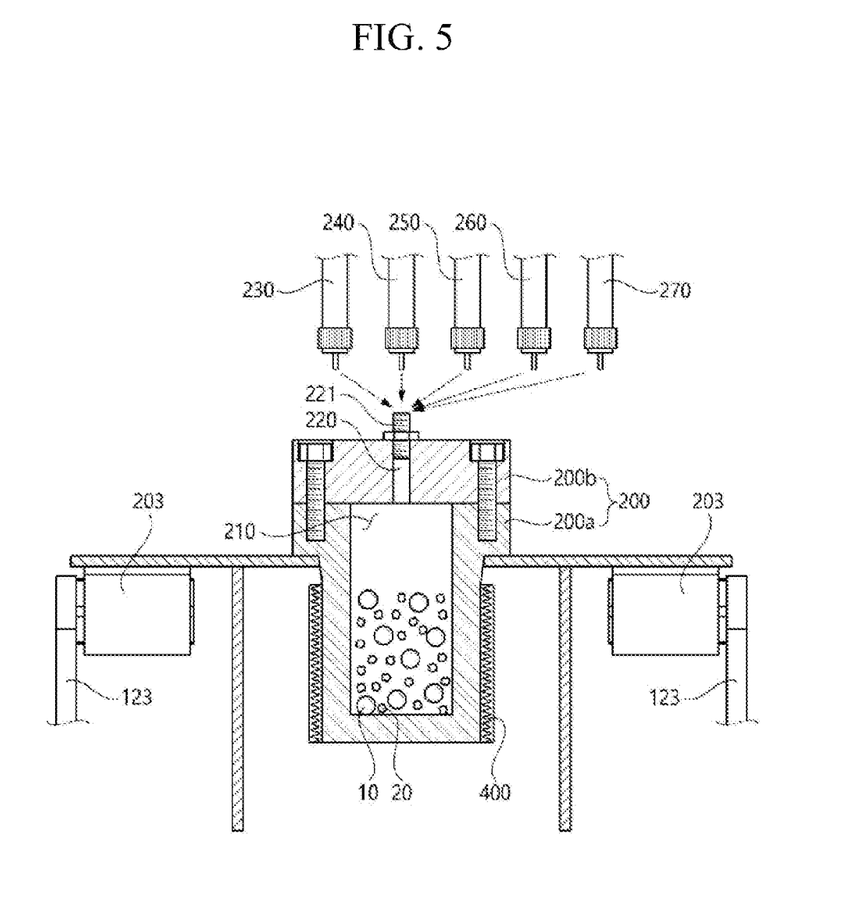
FIG. 5 is a cross-sectional view showing the configuration of a canister in the shale gas extracting device according to the present invention.

In addition, as shown in FIG. 5, the heating means 400 is made of a heating coil wound around the outside of the canister 200. The heating coil is preferable to be covered for safety.

In this case, it is preferable that the wires connected to the heating means 400 are connected to the base 100 through the installed canister support 120.

Figure 4:
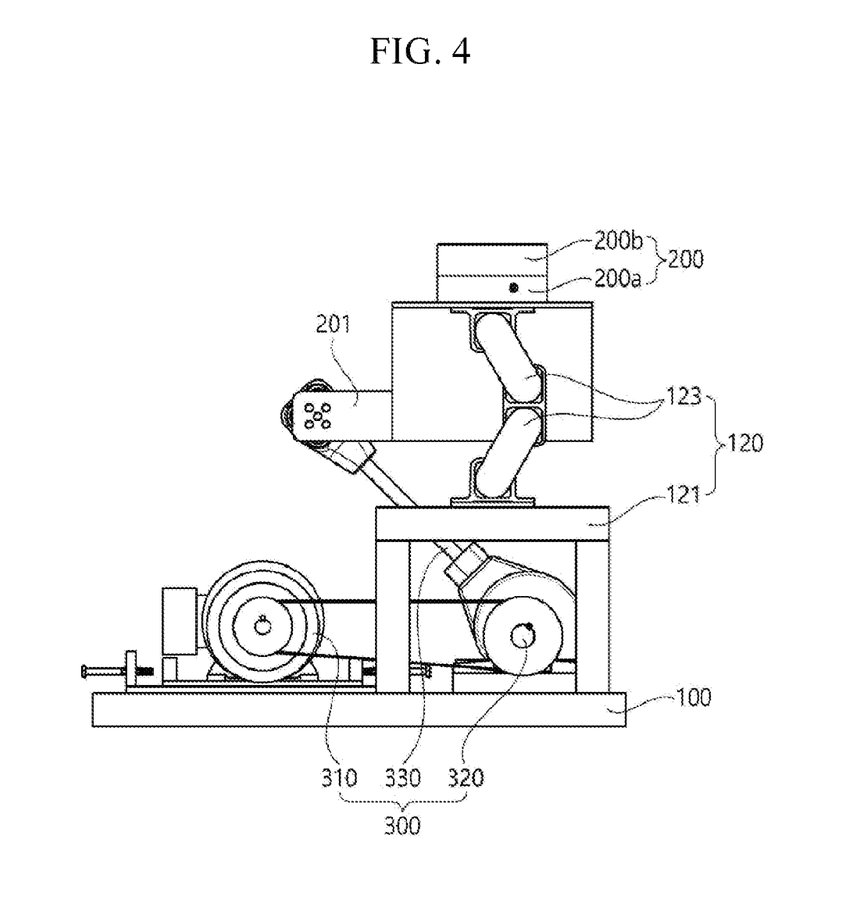
FIG. 4 is a side view showing a shale gas extracting device according to the present invention.
Figure 6:
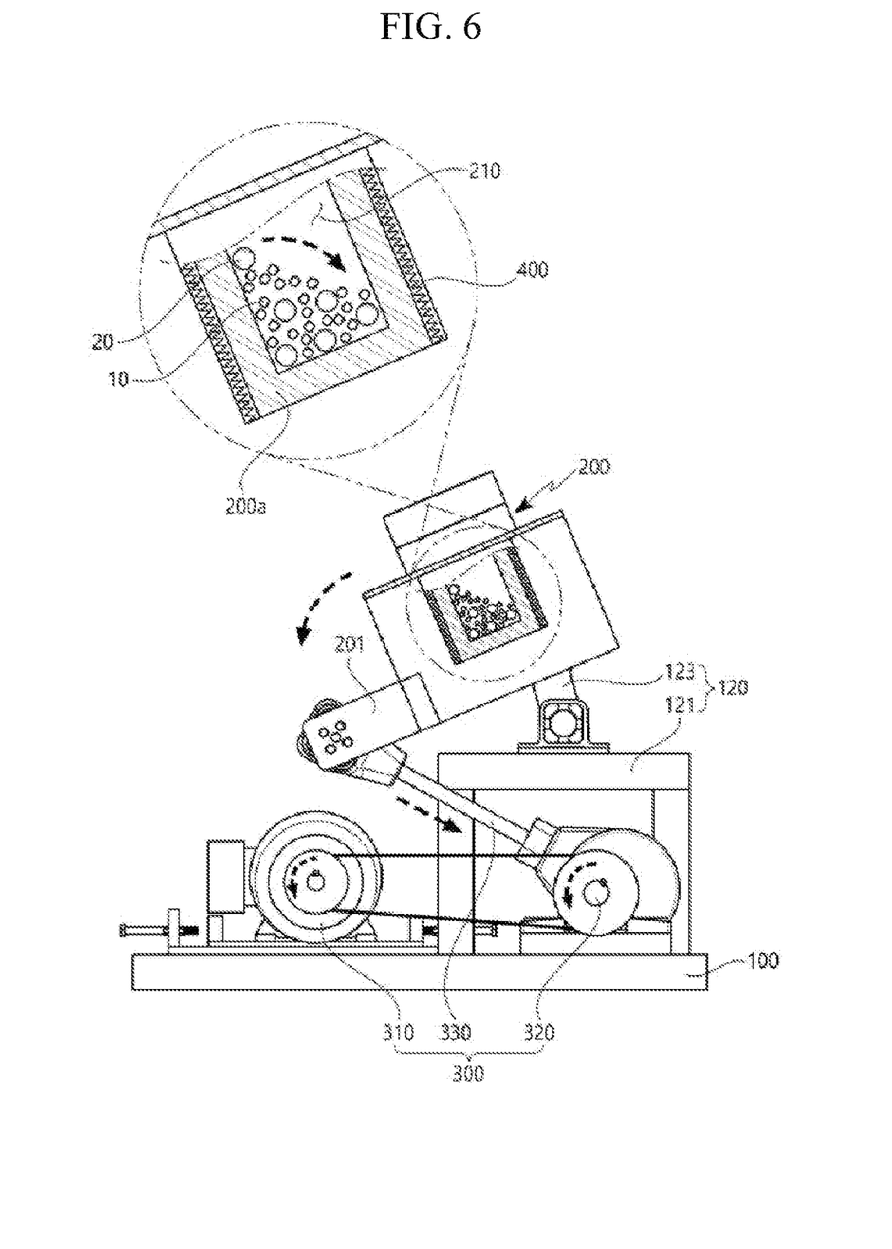
FIGS. 6 and 7 is an operating state diagram showing the process for crushing the rock sample by the driving means in the shale gas extracting device according to the present invention.
Figure 7:
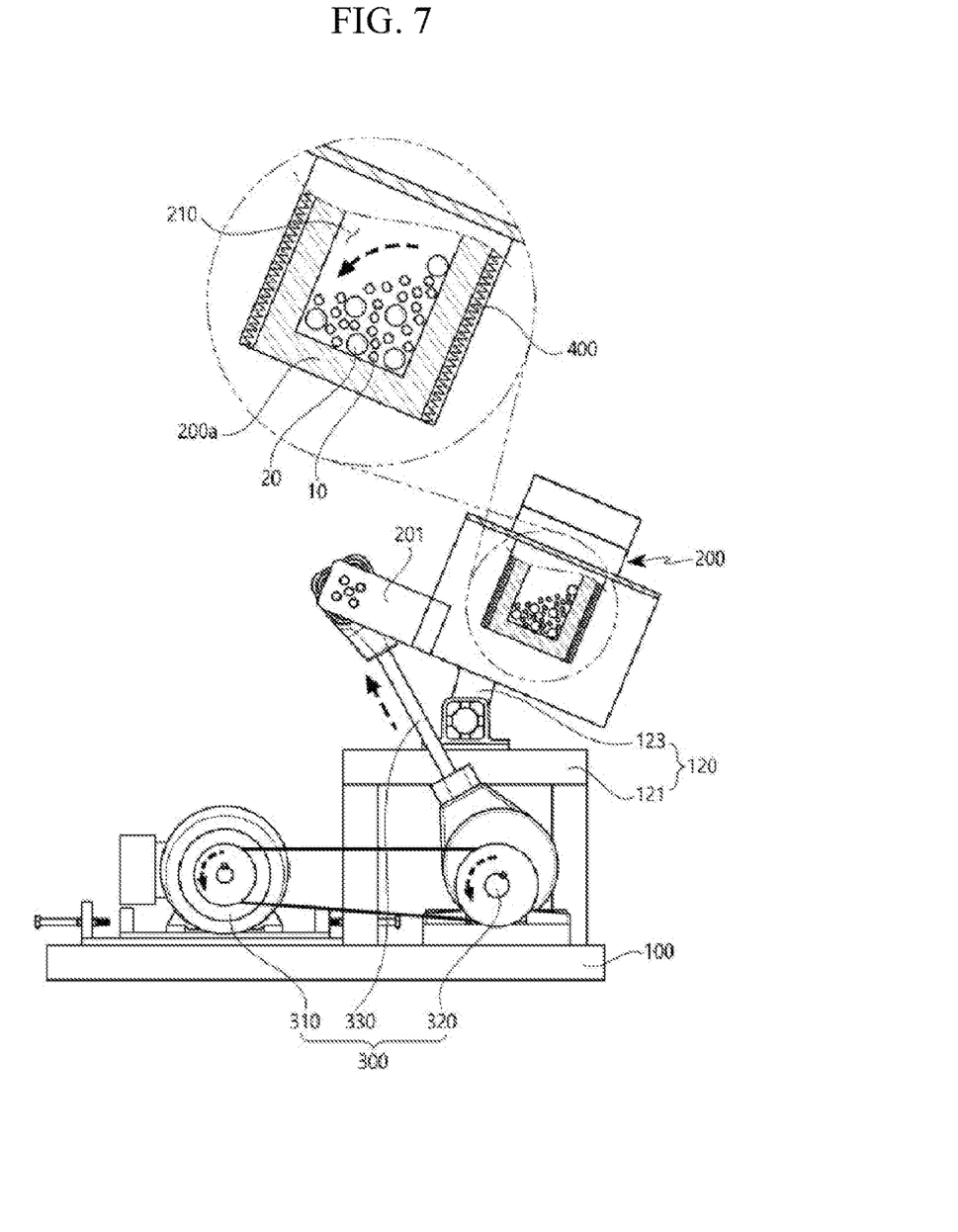

In addition, as shown in FIGS. 4, 6 and 7, the rock sample 10 is crushed by mixing with the ball mill 20 received in the canister 200 by oscillating the canister 200 driven by the driving means 300.

In this case, the driving means 300 is installed in the base 100. The driving motor 310 with a rotational power is provided. The crankshaft 320, which is connected to the driving motor 310 to rotate, is installed to be adjacent to the drive motor 310 in the base 100.

Then, a connecting rod 330 is connected to the bracket 201 formed in the lower portion of the canister 200 and the crank shaft 320. The connecting rod 330 oscillates the canister 200 through the rotation of the crank shaft 320.

In addition, the injection port 220 of the canister 200 includes a vacuum tube 230, a pressure tube 240, a sensor tube 250, an injection tube 260, and an extracting tube 270 that are sequentially detached.

Here, the vacuum tube 230 is detachably connected to the injection port 220 of the canister 200 so as to suck and remove an atmospheric gas in the receiving space 210 of the canister 200 to evacuate.

This eliminates all impurities that impede the extraction of shale gas from the receiving space 210 for accurate measurement when the rock sample 10 is injected into the receiving space 210.

Next, the pressure tube 240 is detachably connected to the inlet 220 of the canister 200 to inject nitrogen gas into the receiving space 210 of the canister 200 to increase the internal pressure.

At this time, the heating means 400 such as a heating coil heat the canister 200, thereby the pressure rises by the nitrogen gas injection and the temperature rises by the heating. Then, environmental conditions of rock samples 10 buried in the shale layer is provided.

Next, the sensor tube 250 is connected to the injection port 220 to check the pressure and temperature of the receiving space 210 through the sensor of the sensor tube 250. The temperature can further rise by reconnecting the pressure tube 240 or through the heating means 400 if necessary.

Meanwhile, the injection tube 260 is detachably connected to the injection port 220 of the canister 200. A supersaturated sodium chloride (Nacl) solution (hereinafter, it is referred to be as a saturated solution) is injected into the receiving space 210 of the canister 200.

This prevents the shale gas from reattaching to the rock sample 10 by filling the voids of the rock sample 10 with the saturated solution. The voids can be small holes or gaps from which the shale gas has escaped.

On the other hand, the extracting tube 270 is detachably connected to the injection port 220 of the canister 200 to suction and collect the shale gas separated from the rock sample 10.

In addition, it is preferable that the injection port 220 is further provided with a check valve 221 to prevent leakage of the materials and pressure received and injected into the receiving space 210.

That is, the vacuum tube 230, the pressure tube 240, the sensor tube 250, the injection tube 260, and the extracting tube 270 are sequentially attached to or detached from the injection port 220 in a replacing manner. The canister 200 is independently operated from each tube by performing the necessary operation.

Figure 8:
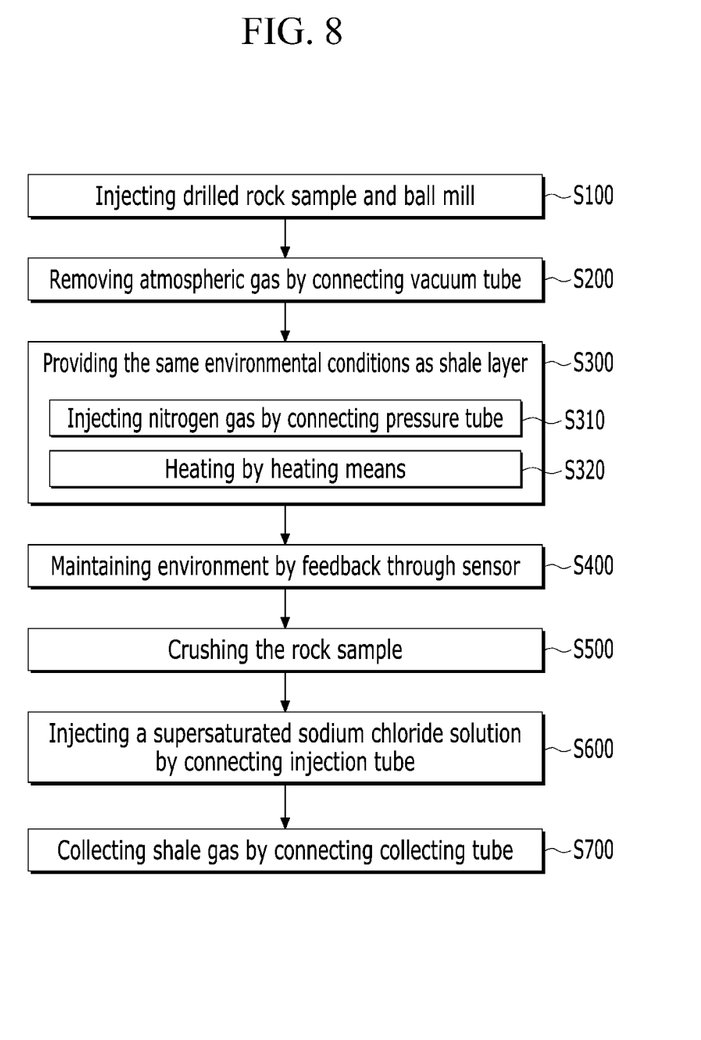
FIG. 8 is a flowchart illustrating a shale gas extracting method according to the present invention.

As shown in FIG. 8, using the shale gas extracting device of the present invention configured as described above, the shale gas is collected by step of injecting S100, step of removing S200, step of providing S300, step of maintaining S400, step of crushing S500, step of injecting S600, and step of extracting S700.

First, the step of injecting S100 is to separate the canister 200 into the body 200a and a lid 200b, and then input the drilled rock sample 10 into the receiving space 210. The rock sample 10 is hermetically received in the canister 200 by closing the lid 200b.

That is, while the conventional rod mill is limited within the rotational movement, a plurality of ball mills 20 having a metal ball shape applied to the present invention crush rock samples of the sedimentary rock into fine particles by oscillating the canister 200.

Next, in the step of removing S200, the vacuum tube 230 is connected to the injection port 220 of the canister 200 in which the rock sample 10 and the ball mill 20 are hermetically sealed, and then atmospheric gas in the canister 200 is removed.

Next, the step of providing S300 includes steps of pressurizing S310 and heating S320 so as to provide an environment which is similar to the time of burial for the drilled rock sample 10.

In the step of pressurizing S310, the pressure tube 240 is connected to the injection port 220 of the canister 200, and the nitrogen gas is injected into the receiving space 210 of the canister 200 to increase the pressure.

In addition, in the step of heating S320, the receiving space 210 of the canister 200 is heated through the heating means 400 provided on the outside of the canister 200.

That is, through the steps of pressurizing S310 and heating S320, the inside of the canister 200 is provided with the same environmental conditions as the shale layer.

Next, in the step of maintaining S400, the sensor tube 250 having a variety of sensors is connected to the injection port 220 to measure the internal pressure and temperature of the receiving space 210. Then, they are provided to the control device or are displayed in order to maintain the optimal environment for the workers.

Next, in the step of crushing S500, the rock sample 10 is crushed with the ball mills 20 by driving the drive means 300 and oscillating the canister 200.

In other words, the rotational driving force of the driving motor 310 of the driving means 300 rotates the crank shaft 320 connected through the belt. In this case, the connecting rod 330 connected to the crank shaft 320 converts a rotational movement of the shaft 320 into a linear movement.

At this time, as one end of the connecting rod 330 is connected to the rotatably supported bracket 201 formed in the canister 200, the canister 200 is oscillated while being swung up and down repeatedly.

That is, as shown in FIG. 6, the connecting rod 330 is pulled back by the crankshaft 320 to pull the bracket 201 and the canister 200 is rotated in the downward direction to mix the rock sample 10 and the ball mill 20. Conversely, as shown in FIG. 7, as the connecting rod 330 moves forward by the crankshaft 320 and then the bracket 201 is pushed out, the canister 200 rotates in the upward direction and the rock sample 10 and the ball mill 20 are mixed together, thereby the rock sample 10 is crushed by the ball milling.

Next, in the step of injecting S600, injection tube 260 is connected to the injection port 220 of the canister 200 and a saturated solution made of supersaturated sodium chloride is injected into the canister 200. The shale gas is further separated from the rock sample 10 through the saturated solution penetrating into the voids of the rock sample 10.

Finally, in the step of collecting S700, the extracting tube 270 is connected to the injection port 220 of the canister 200 to collect the shale gas separated from the rock sample 10 and then transmit it to a measuring device.

By the present invention configured as described above, the amount of shale gas collected from the drilled rock sample 10 can be analyzed to determine the exact reserve of the reservoir. As the structure of the shale gas extracting device is changed into the inducing manner which is different from the conventional rotational manner, there is an effect of securing profitability by minimizing the volume.

The terms and words used in the present specification and claims described above should not be construed as being limited to the ordinary or dictionary meanings, and the inventors should use the terms of the term in order to explain their invention in the best way. Based on the principle that the concept can be properly defined, it should be interpreted as meaning and concept corresponding to the technical idea of the present invention.

INDUSTRIAL APPLICABILITY

The present invention relates to a shale gas extracting device including a canister installed on a canister support vertically installed on both sides of a base so as to be vertically rotatable, forming a receiving space for hermetically receiving the drilled rock sample and the ball mill together and having an injection port at one side of an upper end of the canister; driving means oscillating the canister 200 so that the rock sample is crushed by mixing with the ball mill accommodated in the canister; heating means heating the canister; and a vacuum tube, a pressure tube, a sensor tube, an injection tube, and a collecting tube sequentially detached and coupled to the injection port of the canister. A method for extracting shale gas using the above-identified shale gas extracting device includes a step of injecting the drilled rock sample and the ball mill together into the receiving space of the canister and hermetically receiving the drilled rock sample and the ball mill; a step of removing the atmospheric gas in the canister by connecting the vacuum tube to the injection port of the canister; a step of providing the same environmental conditions as the shale layer with an inside of the canister; a step of maintaining an internal environment of the canister by feedback through a sensor connected to the canister; a step of crushing the rock sample with the ball mill by oscillating the canister which is driven by the driving means; a step of injecting a supersaturated sodium chloride solution into the canister by connecting the injection tube to the injection port of the canister; and a step of collecting the shale gas separated from the rock sample by connecting the extracting tube to the injection inlet of the canister. Then, extracting amount of the shale gas is analyzed and accurate reserves of the reservoir can be confirmed. As the structure of the shale gas extracting device is changed into the inducing manner which is different from the conventional rotational manner, and a volume thereof is minimized to secure profitability, thereby applicability in a field of extracting the shale gas can be secured.

The invention claimed is:

1. A shale gas extracting device comprising:
   a canister 200 installed on canister supports 120 vertically installed on ends of a base 100 so as to be vertically rotatable, wherein the canister 200 forms a receiving space 210 for hermetically receiving a drilled rock sample 10 and a ball mill 20 together and has an injection port 220 at one side of an upper end of the canister 200;
   a driver 300 that oscillates the canister 200 so that the rock sample 10 is crushed by mixing with the ball mill 20 accommodated in the canister 200;
   a heater 400 that heats the canister 200; and
   a vacuum tube 230, a pressure tube 240, a sensor tube 250, an injection tube 260, and an extracting tube 270 that are sequentially detached and coupled to the injection port 220 of the canister 200.

2. The device of claim 1, wherein the driver 300 comprises:
   a driving motor 310 that is installed on the base 100 and has a rotational power;
   a crankshaft 320 that is installed in the base 100, adjacent to the driving motor 310 and driven to rotate by being connected to the driving motor 310; and
   a connecting rod 330 that is connected to the crank shaft 320 and a bracket 201 attached on a lower portion of the canister 200 and then is driven by a rotation of the crank shaft 320.

3. The device of claim 1, wherein the vacuum tube 230 is detachably connected to the injection port 220 of the canister 200 so as to suction and remove atmospheric gas and then evacuate the receiving space 210 of the canister 200.

4. The device of claim 1, wherein the pressure tube 240 is detachably connected to the injection port 220 of the canister 200 so as to inject nitrogen gas into the receiving space 210 of the canister 200 and increase an internal pressure of the receiving space 210.

5. The device of claim 1, wherein the injection tube 260 is detachably connected to the injection port 220 of the canister 200 so as to inject a supersaturated sodium chloride solution into the receiving space 210 of the canister 200 and then separate the shale gas from the rock sample 10.

6. The device of claim 1, wherein the extracting tube 270 is detachably connected to the injection port 220 of the canister 200 so as to suction and collect the shale gas separated from the rock sample 10.

7. The device of claim 1 further comprising a check valve 221 that prevents leakage of materials and pressure received and injected into the receiving space 210, the check valve 221 that is installed in the injection port 220.

8. A method for collecting shale gas using the shale gas collection device of claim 1, the method comprising:
   inserting S100 the drilled rock sample 10 and the ball mill 20 together into the receiving space 210 of the canister 200 and hermetically receiving the drilled rock sample 10 and the ball mill 20;
   removing S200 the atmospheric gas in the canister 200 by connecting the vacuum tube 230 to the injection port 220 of the canister 200;
   providing S300 the same environmental conditions as a shale layer with an inside of the canister 200;
   maintaining S400 an internal environment of the canister 200 by feedback through a sensor connected to the canister 200;
   crushing S500 the rock sample 10 with the ball mill 20 by oscillating the canister 200 which is driven by the driver 300;
   injecting S600 a supersaturated sodium chloride solution into the canister 200 by connecting the injection tube 260 to the injection port 220 of the canister 200; and
   collecting S700 the shale gas separated from the rock sample 10 by connecting the extracting tube 270 to the injection inlet 220 of the canister 200.

9. The method of claim 8, wherein the providing S300 comprises:
   pressurizing S310 the receiving space 210 of the canister 200 so as to increase a pressure of the receiving space 210 by connecting the pressure tube 240 to the injection port 220 of the canister 200 and injecting nitrogen gas into the receiving space 210 of the canister 200; and heating S320 the receiving space 210 of the canister 200 through the heater 400 provided outside of the canister 200.

\* \* \* \* \*